United States Patent
Nakayama et al.

(10) Patent No.: US 10,022,051 B2
(45) Date of Patent: Jul. 17, 2018

(54) INFORMATION PROVISION SYSTEM, ELECTRONIC DEVICE, METHOD AND STORAGE MEDIUM

(71) Applicant: TDK Corporation, Minato-ku, Tokyo (JP)

(72) Inventors: Kanako Nakayama, Tokyo (JP); Junya Takakura, Kanagawa (JP); Sawa Fuke, Kanagawa (JP)

(73) Assignee: TDK CORPORATION, Tokyo (JP)

( * ) Notice: Subject to any disclaimer, the term of this patent is extended or adjusted under 35 U.S.C. 154(b) by 200 days.

(21) Appl. No.: 14/564,760

(22) Filed: Dec. 9, 2014

(65) Prior Publication Data

US 2015/0157206 A1 Jun. 11, 2015

(30) Foreign Application Priority Data

Dec. 10, 2013 (JP) ................. 2013-255101

(51) Int. Cl.
 *G08B 1/08* (2006.01)
 *A61B 5/00* (2006.01)
 *A61B 5/0205* (2006.01)
 *G06F 19/00* (2018.01)

(52) U.S. Cl.
 CPC ........ *A61B 5/0015* (2013.01); *A61B 5/02055* (2013.01); *A61B 5/4848* (2013.01); *G06F 19/3418* (2013.01); *G06F 19/3456* (2013.01); *A61B 5/0022* (2013.01); *A61B 2560/029* (2013.01)

(58) Field of Classification Search
 CPC . A61B 5/0015; A61B 5/02055; A61B 5/4848; A61B 5/0022; A61B 2560/029; G06F 19/3418; G06F 19/3456
 USPC ...................................... 340/539.12
 See application file for complete search history.

(56) References Cited

U.S. PATENT DOCUMENTS

| 6,198,952 B1 * | 3/2001 | Miesel ................. A61B 5/1459 600/333 |
| 2005/0228242 A1 | 10/2005 | Kawamura et al. |
| 2006/0129202 A1 * | 6/2006 | Armstrong ............... A61B 5/01 607/45 |
| 2006/0183980 A1 * | 8/2006 | Yang .................... A61B 5/6804 600/301 |
| 2007/0135691 A1 | 6/2007 | Zingelewicz et al. |

(Continued)

FOREIGN PATENT DOCUMENTS

| JP | 2002-345759 | 12/2002 |
| JP | 2005-168834 | 6/2005 |

(Continued)

*Primary Examiner* — Naomi J Small
(74) *Attorney, Agent, or Firm* — Oliff PLC (57) ABSTRACT

According to one embodiment, an information provision system including a biological sensor device including a sensor and an information transmitting terminal communicably connected to the biological sensor device is provided. The information transmitting terminal includes a detector. The detector detects an action of the user. The biological sensor device includes an obtaining module. The obtaining module obtains, when the action of the user is detected, biological data by driving the sensor during a measurement period included in a measurement information in association with the action.

18 Claims, 7 Drawing Sheets

| Symptom | Medication (type) | Measurement item | Sensor | Measurement period | Sampling interval |
|---|---|---|---|---|---|
| High blood pressure | Diuretic | Blood pressure | Electrocardiogram, pulse wave | 1h | Electrocardiogram (1 ms), pulse wave (8 ms) |
| | Aldosterone blocker | Blood pressure | Electrocardiogram, pulse wave | 9h | Electrocardiogram (1 ms), pulse wave (8 ms) |
| | β blocker | Blood pressure, heart rate reduction | Electrocardiogram, pulse wave | 5h | Electrocardiogram (1 ms), pulse wave (8 ms) |
| | α receptor blocker | Blood pressure, skin temperature increase | Electrocardiogram, pulse wave, thermometer | 12h | Electrocardiogram (1 ms), pulse wave (8 ms), temperature (10 minutes) |
| | Renin-angiotensin system | Blood pressure, dry cough | Electrocardiogram, pulse wave, acceleration (microphone) | 2h | Electrocardiogram (1 ms), pulse wave (8 ms), acceleration (8 ms) |
| Bradycardia | β 1 irritant | Heart rate, skin temperature increase | Electrocardiogram (pulse wave), thermometer | 12h | Electrocardiogram (8 ms), temperature (30 minutes) |
| | Atropine (anticholinergic medication) | Heart rate, autonomic activity | Electrocardiogram (pulse wave) | 4h | Electrocardiogram (8 ms) |
| Arrhythmia | Antiarrhythmic medication | Heart rate | Electrocardiogram (pulse wave) | 10h | Electrocardiogram (8 ms) |
| Insomnia | Melatonin receptor agonist | Asleep condition | Electrocardiogram (pulse wave) | 2h | Electrocardiogram (8 ms), acceleration (8 ms) |
| | Benzodiazepine | Asleep condition | Electrocardiogram (pulse wave) | 10h | Electrocardiogram (8 ms), acceleration (8 ms) |
| | Nonbenzodiazepine | Asleep condition | Electrocardiogram (pulse wave) | 6h | Electrocardiogram (8 ms), acceleration (8 ms) |

(56) References Cited

U.S. PATENT DOCUMENTS

| | | | |
|---|---|---|---|
| 2008/0055069 A1* | 3/2008 | Aiki | H04W 52/029 340/539.3 |
| 2008/0284599 A1* | 11/2008 | Zdeblick | A61B 5/0031 340/572.1 |
| 2008/0306359 A1 | 12/2008 | Zdeblick et al. | |
| 2011/0202365 A1 | 8/2011 | Khanuja | |
| 2011/0273839 A1* | 11/2011 | Villegas | A61B 5/0002 361/679.41 |
| 2011/0295083 A1* | 12/2011 | Doelling | A61B 5/103 600/301 |
| 2012/0004520 A1 | 1/2012 | Whitworth et al. | |
| 2012/0004527 A1 | 1/2012 | Thompson et al. | |
| 2012/0007734 A1 | 1/2012 | Berkman et al. | |
| 2012/0024889 A1 | 2/2012 | Robertson et al. | |
| 2012/0062379 A1 | 3/2012 | Hafezi et al. | |
| 2012/0116188 A1 | 5/2012 | Frank et al. | |
| 2012/0179067 A1* | 7/2012 | Wekell | A61B 5/0002 600/587 |
| 2012/0299723 A1 | 11/2012 | Hafezi et al. | |
| 2013/0053657 A1 | 2/2013 | Ziarno et al. | |
| 2013/0303869 A1* | 11/2013 | Rebec | A61B 5/14532 600/365 |
| 2014/0171039 A1* | 6/2014 | Bjontegard | H04W 4/029 455/414.1 |
| 2016/0147951 A1* | 5/2016 | Francois | G06Q 50/24 705/3 |
| 2017/0000180 A1 | 1/2017 | Arne et al. | |

FOREIGN PATENT DOCUMENTS

| | | |
|---|---|---|
| JP | 2005-319283 A | 11/2005 |
| JP | 2007-175263 A | 7/2007 |
| JP | 2007-188149 | 7/2007 |
| JP | 2008-539047 | 11/2008 |
| JP | 2009-519514 A | 5/2009 |
| JP | 2010-057552 A | 3/2010 |
| JP | 2010-125145 A | 6/2010 |

* cited by examiner

| Symptom | Medication (type) | Measurement item | Sensor | Measurement period | Sampling interval |
|---|---|---|---|---|---|
| High blood pressure | Diuretic | Blood pressure | Electrocardiogram, pulse wave | 1h | Electrocardiogram (1 ms), pulse wave (8 ms) |
| | Aldosterone blocker | Blood pressure | Electrocardiogram, pulse wave | 9h | Electrocardiogram (1 ms), pulse wave (8 ms) |
| | β blocker | Blood pressure, heart rate reduction | Electrocardiogram, pulse wave | 5h | Electrocardiogram (1 ms), pulse wave (8 ms) |
| | α receptor blocker | Blood pressure, skin temperature increase | Electrocardiogram, pulse wave, thermometer | 12h | Electrocardiogram (1 ms), pulse wave (8 ms), temperature (10 minutes) |
| | Renin-angiotensin system | Blood pressure, dry cough | Electrocardiogram, pulse wave, acceleration (microphone) | 2h | Electrocardiogram (1 ms), pulse wave (8 ms), acceleration (8 ms) |
| Bradycardia | β 1 irritant | Heart rate, skin temperature increase | Electrocardiogram (pulse wave), thermometer | 12h | Electrocardiogram (8 ms), temperature (30 minutes) |
| | Atropine (anticholinergic medication) | Heart rate, autonomic activity | Electrocardiogram (pulse wave) | 4h | Electrocardiogram (8 ms) |
| Arrhythmia | Antiarrhythmic medication | Heart rate | Electrocardiogram (pulse wave) | 10h | Electrocardiogram (8 ms) |
| Insomnia | Melatonin receptor agonist | Asleep condition | Electrocardiogram (pulse wave) | 2h | Electrocardiogram (8 ms), acceleration (8 ms) |
| | Benzodiazepine | Asleep condition | Electrocardiogram (pulse wave) | 10h | Electrocardiogram (8 ms), acceleration (8 ms) |
| | Nonbenzodiazepine | Asleep condition | Electrocardiogram (pulse wave) | 6h | Electrocardiogram (8 ms), acceleration (8 ms) |

INFORMATION PROVISION SYSTEM, ELECTRONIC DEVICE, METHOD AND STORAGE MEDIUM

CROSS-REFERENCE TO RELATED APPLICATIONS

This application is based upon and claims the benefit of priority from Japanese Patent Application No. 2013-255101, filed Dec. 10, 2013, the entire contents of which are incorporated herein by reference.

FIELD

Embodiments described herein relate generally to an information provision system, an electronic device, a method and a storage medium which provide biological data related to a user.

BACKGROUND

In general, patients suffering from a symptom of a physical disease take medication to alleviate the symptom.

For example, after a doctor prescribes a medication for a patient, the doctor or patient may confirm whether or not the medication is working.

In recent years, biological sensors which are worn by a user to obtain his/her biological data have been developed. As the biological data, for example, an electrocardiogram (heartbeat interval), pulse wave, body temperature and body movement (acceleration) of the user are obtainable by the sensors.

The biological data obtained by such sensors can be offered to doctors or patients as information necessary to determine whether or not the effect of the taken medication is manifest.

In order for a doctor or patient to accurately determine whether or not the effect of the taken medication is manifest, it is desirable to provide the doctor or patient with biological data which is obtained at all times by a biological sensor.

However, since biological sensors are worn by patients in use as stated above, the sensors need to be reduced in weight and size. Thus, in biological sensors, it is difficult to ensure power necessary to continue to always obtain biological data.

BRIEF DESCRIPTION OF THE DRAWINGS

FIG. 5 shows an example of the data structure of measurement information held in a controller 22 shown in FIG. 4.

DETAILED DESCRIPTION

In general, according to one embodiment, an information provision system including a biological sensor device including a sensor and an information transmitting terminal communicably connected to the biological sensor device. The information transmitting terminal includes a detector. The detector detects an action of the user. The biological sensor device includes a memory and an obtaining module. The memory holds measurement information including a measurement period during which biological data is obtained in association with the action of the user. The obtaining module obtains, when the action of the user is detected, biological data by driving the sensor during the measurement period included in the measurement information in association with the action.

Embodiments will be described hereinafter with reference to the accompanying drawings.

Figure 1:
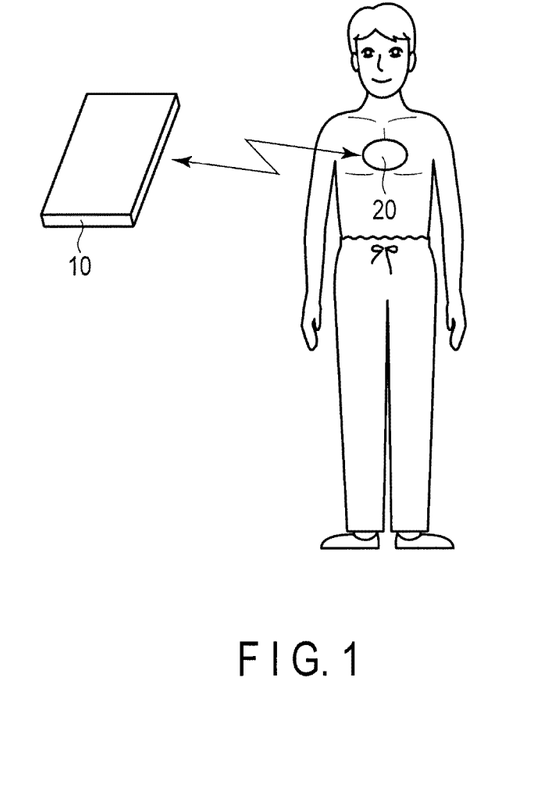
FIG. 1 shows a structure of an information provision system according to an embodiment.

FIG. 1 shows a structure of an information provision system according to an embodiment. The information provision system of the embodiment is used for providing a doctor or a patient (user) on medication with biological data related to the patient as information which is necessary for the doctor or patient to determine whether or not the medication is actually working for the patient.

As shown in FIG. 1, the information provision system includes an information transmitting terminal (electronic device) 10 used by the user (patient) on medication, etc., and a biological sensor device 20 worn by the user.

In the present embodiment, the information transmitting terminal 10 is realized as a mobile electronic device such as a tablet computer or a smartphone. The information transmitting terminal 10 shown in FIG. 1 is assumed to be a tablet computer.

The biological sensor device 20 is a compact, lightweight and thin device driven by a battery (for example, a built-in secondary battery). The biological sensor device 20 is attached to, for example, the breast of the user by an adhesive tape in use. Apart from the attachment to the breast, the biological sensor device 20 may be worn as a wristband or earphones. The biological sensor device 20 includes a plurality of types of sensors capable of measuring the electrocardiogram (heartbeat interval), pulse wave, body temperature, body movement (acceleration) and the like. By driving these sensors, the biological sensor device 20 can obtain biological data related to the user.

The information transmitting terminal 10 is communicably connected to biological sensor device 20. Thus, the biological data obtained by the biological sensor device 20 as described above can be offered to the user and the like through the information transmitting terminal 10. The information transmitting terminal 10 communicates with the biological sensor device 20 by using, for example, Bluetooth (registered trademark). The communication between the information transmitting terminal 10 and the biological sensor device 20 is not limited to wireless communication, and may be wired communication.

The biological sensor device 20 includes a plurality of sensors in order to simultaneously obtain a plurality of biological data items. Since the specifications of analogue front-ends of the sensors differ depending on each sensor, combination of flexibility and high-performance is required. Thus, the size of the biological sensor device 20 is enlarged. However, in the present embodiment, a plurality of analog front-ends and CPUs are accumulated on a single chip by using the pseudo-SoC technology. This accumulation realizes a sensor module which is several millimeters square. The pseudo-SoC technology is a technique which realizes both miniaturization equivalent to SoC and designing flexibility equivalent to SiP by accumulating components on a wafer. By connecting a small number of peripheral components such as an antenna and a battery to the module, the biological sensor device 20 is realized as a compact, lightweight (substantially dozen grams) and thin (substantially several millimeters) device. In the above explanations, the size of the biological sensor device 20 is reduced by using the pseudo-SoC technology. However, the biological sensor device 20 may be downsized by using, for example, LSI.

Figure 2:
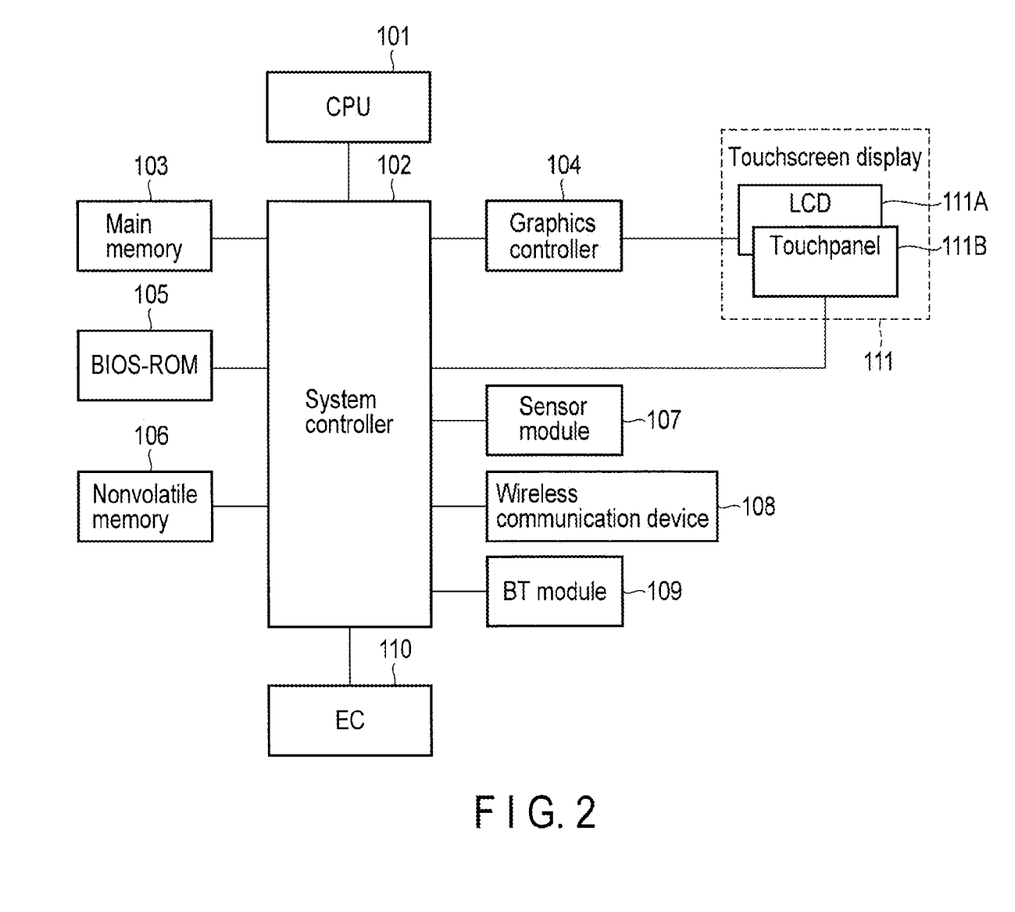
FIG. 2 shows a system configuration of an information transmitting terminal 10 shown in FIG. 1.

FIG. 2 shows a system configuration of the information transmitting terminal (tablet computer) 10 shown in FIG. 1.

As shown in FIG. 2, the information transmitting terminal 10 includes a CPU 101, a system controller 102, a main memory 103, a graphics controller 104, a BIOS-ROM 105, a nonvolatile memory 106, a sensor module 107, a wireless communication device 108, a BT module 109, an EC 110 and a display 111, etc.

The CPU 101 is a processor configured to control the operation of each component of the information transmitting terminal 10. The CPU 101 executes various types of software loaded from the nonvolatile memory 106 which is a storage device to the main memory 103. The software includes an operating system (OS) and various application programs.

The CPU 101 also executes a basic input/output system (BIOS) stored in the BIOS-ROM 105. The BIOS is a program for hardware control.

The system controller 102 is a device configured to connect a local bus of the CPU 101 and various components. A memory controller configured to control the access to the main memory 103 is built into the system controller 102. The system controller 102 has a function for executing communication with the graphics controller 104 through a serial bus compatible with PCI EXPRESS standards.

The graphics controller 104 is a display controller configured to control an LCD 111A used as the touchscreen display 111 of the information transmitting terminal 10. A display signal produced by the graphics controller 104 is sent to the LCD 111A. The LCD 111A displays a screen image based on the display signal. A touchpanel 111B is, for example, a capacitance-type pointing device for inputting data on the screen of the LCD 111A. For example, the touchpanel 111B detects the contact position of a finger of the user on the screen, and the movement of the position. By the touchpanel 111B, the graphical user interface (GUI) displayed on the screen of the LCD 111A can be operated.

The sensor module 107 includes various types of sensors and obtains signals (information) detected by the sensors. The sensors mounted on the sensor module 107 includes an acceleration sensor configured to detect the acceleration of the information transmitting terminal 10, a microphone configured to convert the sound around the information transmitting terminal 10 into an electric signal, and a thermometer configured to measure the air temperature around the information transmitting terminal 10.

The wireless communication device 108 is a module configured to execute wireless communication by a wireless LAN or 3G mobile communication, etc. The wireless communication device 108 enables the information transmitting terminal 10 to wirelessly communicate with, for example, an external server device via a wireless LAN.

The BT module 109 is a module configured to execute wireless communication with a device compatible with Bluetooth by using Bluetooth. The BT module 109 enables the information transmitting terminal 10 to wirelessly communicate with, for example, the biological sensor device 20 via Bluetooth.

The EC 110 is a power management controller for managing power of the information transmitting terminal 10.

Figure 3:
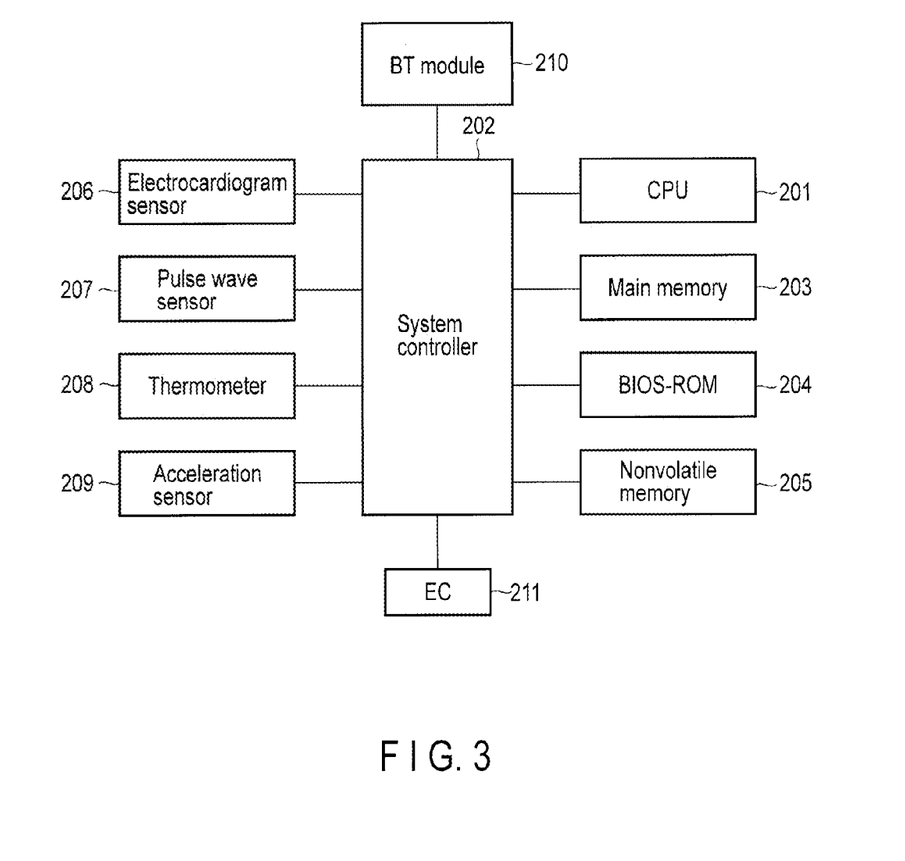
FIG. 3 shows a system configuration of a biological sensor device 20 shown in FIG. 1.

FIG. 3 shows a system configuration of the biological sensor device 20 shown in FIG. 1. As shown in FIG. 3, the biological sensor device 20 includes a CPU 201, a system controller 202, a main memory 203, a BIOS-ROM 204, a nonvolatile memory 205, an electrocardiogram sensor 206, a pulse wave sensor 207, a thermometer 208, an acceleration sensor 209, a BT module 210 and an EC 211, etc.

The CPU 201 is a processor configured to control the operation of each component of the biological sensor device 20. The CPU 201 executes various types of software loaded from the nonvolatile memory 205 which is a storage device to the main memory 203.

The system controller 202 is a device configured to connect a local bus of the CPU 201 and various components. For example, the CPU 201, the main memory 203, the BIOS-ROM 204, the nonvolatile memory 205, the electrocardiogram sensor 206, the pulse wave sensor 207, the thermometer 208, the acceleration sensor 209, the BT module 210 and the EC 211 are connected to the system controller 202.

The electrocardiogram sensor 206 is a sensor for measuring the electrocardiogram of the user as a biological signal. The electrocardiogram sensor 206 is capable of measuring, for example, the electrocardiographic waveform and heartbeat interval (heart rate). The pulse wave sensor 207 is a sensor for measuring the pulse wave of the user as a biological signal. The pulse wave sensor 207 is capable of measuring, for example, the pulse waveform and pulse interval (pulse rate). The thermometer 208 is a sensor for measuring the body temperature (the temperature of the body surface) of the user as a biological signal. The acceleration sensor 209 is a sensor for measuring the body movement (acceleration) of the user as a biological signal.

Sensors other than the sensors 206 to 209 (for example, a microphone) may be provided in the biological sensor device 20.

The BT module 210 is a module configured to execute wireless communication with a device compatible with Bluetooth by using Bluetooth. The BT module 210 enables the biological sensor device 20 to wirelessly communicate with, for example, the information transmitting terminal 10 via Bluetooth.

The EC 211 is a power management controller for managing power of the biological sensor device 20.

Figure 4:
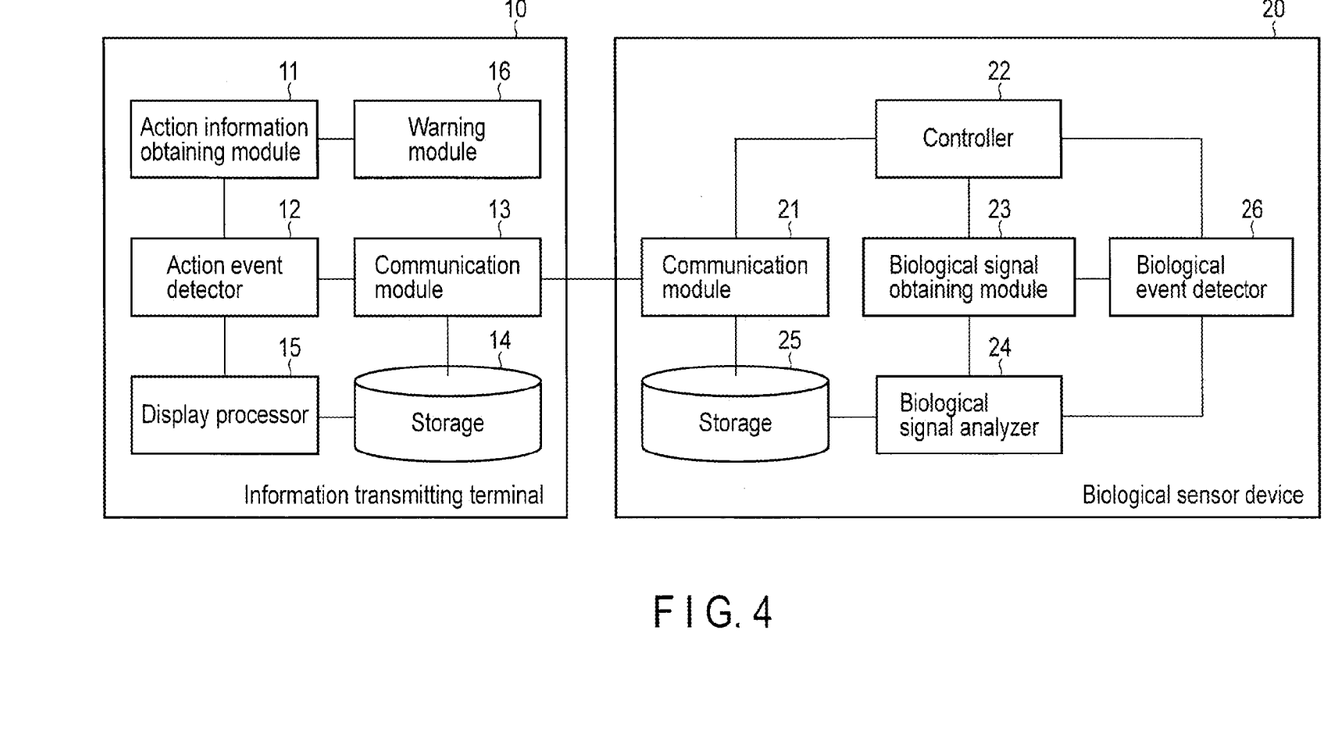
FIG. 4 is a block diagram mainly showing a functional configuration of the information provision system according to the embodiment.

FIG. 4 is a block diagram mainly showing a functional configuration of the information provision system according to the present embodiment.

As shown in FIG. 4, the information transmitting terminal 10 includes an action information obtaining module 11, an action event detector 12, a communication module 13, a storage 14, a display processor 15 and a warning module 16.

The action information obtaining module 11 obtains information related to the action of the user of the information transmitting terminal 10 (hereinafter, referred to as action information). The action information is information used for detecting action events described later. The action information may be obtained in response to a predetermined operation by the user on the information transmitting terminal 10, or may be obtained by using the above-described sensors included in the sensor module 107.

The action event detector 12 detects an action event based on the action information obtained by the action information obtaining module 11. The action events detected by the action event detector 12 include an event in which the user took medication.

The communication module 13 is a functional module for executing Bluetooth communication with the biological sensor device 20. The communication module 13 transmits the action event (for example, intake of medication by the user) detected by the action event detector 12 to the biological sensor device 20. In other words, the communication module 13 notifies the biological sensor device 20 of the action event detected by the action event detector 12.

The communication module 13 receives biological data transmitted by the biological sensor device 20 as explained later. The biological data received by the communication module 13 is accumulated (stored) in the storage 14.

The display processor 15 displays the biological data stored in the storage 14 in the display 111 in response to an instruction of the user (or doctor) on the information transmitting terminal 10. In this manner, the biological data of the user is offered to the user (or a doctor, etc.) as information necessary to confirm whether or not the medication is actually working as described above.

When a predetermined action event (for example, intake of medication by the user) is not detected by the action event detector 12 within a predetermined period, the warning module 16 outputs a warning to the user, indicating that the user has forgotten to take his/her medication.

As shown in FIG. 4, the biological sensor device 20 includes a communication module 21, a controller 22, a biological signal obtaining module 23, a biological signal analyzer 24, a storage 25 and a biological event detector 26.

The biological sensor device 20 includes the plurality of types of sensors 206 to 209 which are capable of measuring biological signals of the electrocardiogram, pulse wave, body temperature, body movement and the like as described above.

The communication module 21 receives an above-mentioned action event transmitted by the communication module 13 included in the information transmitting terminal 10. The communication module 21 transmits biological data obtained by the biological sensor device 20 to the information transmitting terminal 10 as explained later.

The controller 22 holds information for controlling the measurement of various biological signals by sensors (hereinafter, referred to as measurement information) inside or in an inner table in advance. The measurement information includes measurement periods by the sensors in association with, for example, actions (or action events) of the user. The measurement information is explained in detail later.

Based on the retained (held) measurement information, the controller 22 drives the predetermined sensor during the measurement period included in the measurement information in association with the action event received by the communication module 21 (in other words, the user's action detected in the information transmitting terminal 10).

The biological signal obtaining module 23 obtains the biological signal measured by the sensor which is driven based on the control of the controller 22. The biological signal obtained by the biological signal obtaining module 23 is sent to the biological signal analyzer 24 and the biological event detector 26.

The biological analyzer 24 analyzes the biological signal (raw data) obtained by the biological signal obtaining module 23. In this manner, the biological signal analyzer 24 obtains (produces) information to be offered to the user, etc., or in other words, information which is useful for determining whether or not the effect of the medication is manifest (biological data). Specifically, when the biological signals obtained by the biological signal obtaining module 23 are biological signals of the electrocardiogram and pulse wave, the biological signal analyzer 24 produces, for example, biological data indicating the blood pressure from the biological signals (electrocardiogram and pulse wave). The biological data obtained by the biological signal analyzer 24 is sent to the storage 25 and the biological event detector 26.

The biological data obtained by the biological signal analyzer 24 is stored in the storage 25. The biological data stored in the storage 25 is transmitted to the information transmitting terminal 10 by the communication module 21.

Based on the biological signal obtained by the biological signal obtaining module 23 or the biological data obtained by the biological signal analyzer 24, the biological event detector 26 detects an event related to the living body of the user (hereinafter, referred to as a biological event). The biological events detected by the biological event detector 26 include an event in which the body temperature is high or low, and an event in which the heart rate is increased or decreased. The biological events detected by the biological event detector 26 are informed to the controller 22.

When a biological event detected by the biological event detector 26 is informed to the controller 22, the controller 22 changes, for example, the measurement frequency by the sensors provided in the biological sensor device 20 in accordance with the biological event.

As described above, in the information provision system of the present embodiment, the controller 22 performs control in accordance with an action event and a biological event. By this control, a necessary sensor can be driven only during a necessary period. The control by the controller 22 is explained in detail later.

FIG. 5 shows an example of the data structure of measurement information held in the controller 22 shown in FIG. 4. FIG. 5 shows an example of measurement information for controlling measurement of various biological signals by sensors in a case where the action of the user is intake of medication.

As shown in FIG. 5, measurement information includes a measurement item, a sensor (specifically, sensor information indicating a sensor), a measurement period and a sampling interval in association with each medication (type). In the measurement information shown in FIG. 5, a symptom which should be alleviated by each medication is also shown for convenience.

Each medication indicates the type of medication which is taken to alleviate a symptom.

Each measurement item indicates an item which should be measured (that is, biological data which should be obtained) when a medication associated with the item was taken. Measurement items include a blood pressure and a heart rate, etc.

Each sensor indicates a sensor (or the type of sensor) which should be driven when a medication associated with the sensor was taken. Measurement items can be obtained from biological signals which are obtained by driving the sensor.

Each measurement period indicates a period during which a sensor associated with the period is driven (that is, a period during which biological data is obtained) when a medication associated with the period was taken. Each measurement period is set so as to be sufficient to confirm (observe) whether or not the effect of a medication associated with the period is manifest in a case where the medication was taken.

Each sampling interval indicates a sampling interval of a biological signal by a sensor associated with the interval when a medication associated with the interval was taken.

In sum, the measurement information shown in FIG. 5 includes biological data (measurement item) to be obtained, a sensor to be driven, a measurement period by the sensor and a sampling interval by the sensor in association with each medication (that is, the user's action in which the medication was taken).

The measurement information is now specifically explained with reference to the example shown in FIG. 5. In association with the symptom "high-blood pressure", the measurement information includes the medication "diuretic", the measurement item "blood pressure", the sensors "electrocardiogram" and "pulse wave", the measurement period "1 h" and the sampling intervals "electrocardiogram (1 ms)" and "pulse wave (8 ms)". According to this measurement information, biological data showing the blood pressure is obtained by driving the electrocardiogram sensor 206 and the pulse wave sensor 207 which are provided in the biological sensor device 20 for one hour when diuretic which is a medication for alleviating the symptom "high-blood pressure" was taken. The information also indicates that the sampling intervals of biological signals by the electrocardiogram sensor 206 and the pulse wave sensor 207 in this case are one millisecond and eight milliseconds respectively. The blood pressure (or biological data showing the blood pressure) can be obtained based on the pulse wave velocity based on the feature point (R wave) of electrocardiogram measured by the electrocardiogram sensor 206 and the rising point of the pulse wave measured by the pulse wave sensor 207.

In association with the symptom "bradycardia", the measurement information includes the medication "β1 irritant", the measurement items "heart rate" and "increase in skin temperature", the sensors "electrocardiogram (pulse wave)" and "thermometer", the measurement period "12 h" and the sampling intervals "electrocardiogram (8 ms)" and "temperature (30 minutes)". According to this measurement information, biological data showing the heart rate and the increase in skin temperature is obtained by driving the electrocardiogram sensor 206 (or the pulse wave sensor 207) and the thermometer 208 which are provided in the biological sensor device 20 for twelve hours when β1 irritant which is a medication for alleviating the symptom "bradycardia" was taken. The information also indicates that the sampling intervals of biological signals by the electrocardiogram sensor 206 and the thermometer 208 in this case are eight milliseconds and thirty minutes respectively.

Only the medications "diuretic" and "β1 irritant" are explained above. The above explanations are also applicable to the other medications. Therefore, detailed explanations of the other medications are omitted.

In the above descriptions, FIG. 5 is explained as follows: the measurement information is held in the controller 22 with respect to all of the plurality of types of medications. However, the measurement information may be retained in the controller 22 with respect to only the medication taken by the user (patient) wearing the biological sensor device 20. In this case, the measurement information shown in FIG. 5 (the measurement information of all medications) may be managed in, for example, the information transmitting terminal 10. Only the measurement information of the medication specified by the user (that is, the medication taken by the user) may be obtained from the information transmitting terminal 10, and may be held in the biological sensor device 20 (that is, in the controller 22). When the medication taken by the user is changed, necessary measurement information may be appropriately updated by performing communication between the information transmitting terminal 10 and the biological sensor device 20.

Figure 6:
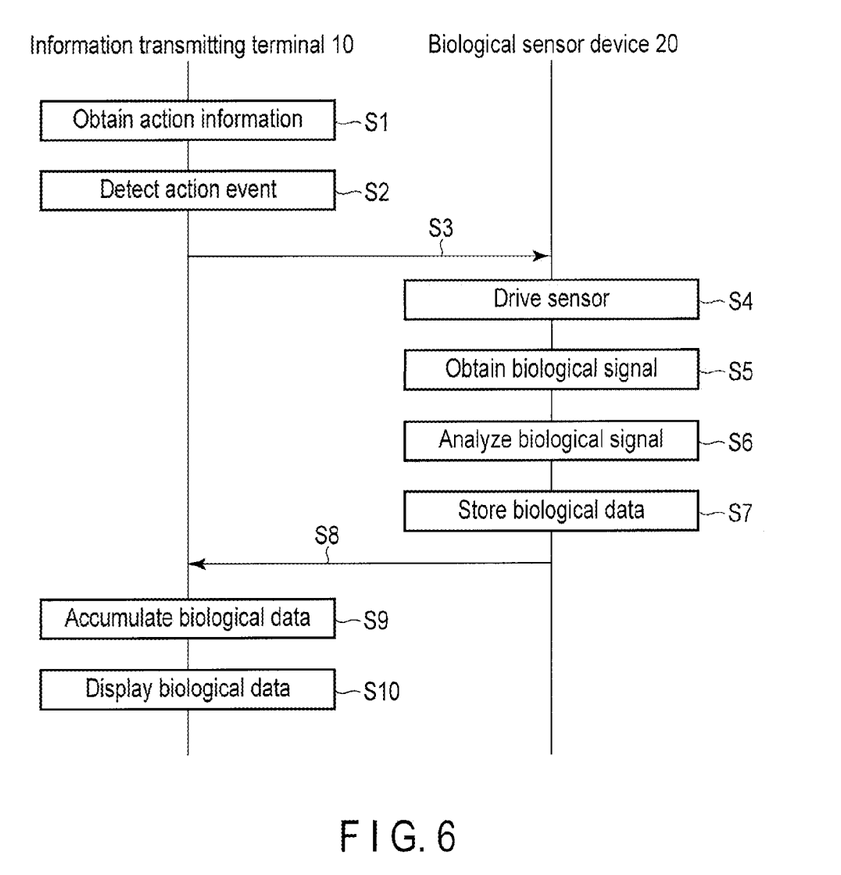
FIG. 6 is a sequence chart showing a procedure of the information provision system according to the embodiment.

This specification now explains a procedure of the information provision system (the information transmitting terminal 10 and the biological sensor device 20) according to the present embodiment, referring to the sequence chart of FIG. 6.

Here, the user wearing the biological sensor device 20 suffers from a high-blood pressure and takes, for example, diuretic as a medication for alleviating the high-blood pressure. Measurement information regarding the medication "diuretic" shown in FIG. 5 (that is, measurement information including the medication "diuretic") is retained in the controller 22 included in the biological sensor device 20.

In the biological sensor device 20, for example, a power saving mode is set. Power consumed by driving various sensors provided in the biological sensor device 20 is kept to the minimum.

In this case, the action information obtaining module 11 included in the information transmitting terminal 10 obtains information (action information) related to the action of the user using the information transmitting terminal 10 (the user wearing the biological sensor device 20) (step S1). The action information obtaining module 11 operates at all times, and obtains, as action information, information in accordance with the operation by the user relative to the information transmitting terminal 10, and information from various sensors provided in the information transmitting terminal 10, such as the acceleration sensor and the microphone.

Here, the action information obtaining module 11 obtains action information in a case where the user took medication (diuretic). The action information indicating that the user took medication includes a predetermined operation (for example, a tap operation) by the user detected in the information transmitting terminal 10. The action information may be information input by using an arbitrary input device, or may be the result of voice recognition processing relative to the voice of the user. In short, in the case where the user took medication, the action information should be information through which the action event detector 12 can detect the user's action (action event) in which the user took medication, as described below.

The action event detector 12 detects the action event based on the action information obtained by the action information obtaining module 11 (step 2). In the case where, as described above, the action information obtaining module 11 obtains action information indicating intake of medication by the user, the action event detector 12 detects the action event in which the user took medication (hereinafter, referred to as "intake event").

The intake event detected by the action event detector 12 is transmitted to the biological sensor device 20 by the communication module 13 (step S3).

The communication module 21 included in the biological sensor device 20 receives the intake event transmitted by the information transmitting terminal 10 (specifically, the communication module 13 included in the information transmitting terminal 10).

After the intake event is received by the communication module 21, the controller 22 drives a sensor(s) provided in the biological sensor device 20 with reference to the measurement information held in the controller 22 (here, the measurement information regarding the medication "diuretic") (step S4).

In this case, the controller 22 drives the sensors (here, the electrocardiogram sensor 206 and the pulse wave sensor 207) included in the measurement information in association with the medication "diuretic" (in other words, the user's action which is the intake of medication "diuretic"). The electrocardiogram sensor 206 and the pulse wave sensor 207 are driven during the measurement period (here, for one hour) included in the measurement information in association with the medication "diuretic".

The biological signal obtaining module 23 obtains biological signals measured by the sensors driven by the controller 22 (step S5). The biological signals are obtained based on the control by the controller 22 in accordance with the sampling intervals included in the measurement information in association with the medication "diuretic". Here, the biological signal by the electrocardiogram sensor 206 is obtained every one millisecond, and the biological signal by the pulse wave sensor 207 is obtained every eight milliseconds.

The biological signal analyzer 24 obtains biological data by analyzing the biological signals obtained by the biological signal obtaining module 23. The biological data is obtained based on the control by the controller 22 in accordance with the measurement item included in the measurement information in association with the medication "diuretic". Here, the biological signal analyzer 24 obtains the biological data which indicates the blood pressure (value) and which is generated from the biological signals by the electrocardiogram sensor 206 and the pulse wave sensor 207.

The biological data obtained by the biological signal analyzer 24 is stored in the storage 25 (step S7). For example, the time when the above-described action event is generated (the time when the action event is detected by the action event detector 12) and the time when the biological data is obtained are added to the biological data stored in the storage 25.

The communication module 21 transmits the biological data stored in the storage 25 to the information transmitting terminal 10 (step S8). The biological data stored in the storage 25 is transmitted when the storage 25 lacks an area for storing biological data obtained while the sensors are driven (in other words, when the storage 25 lacks a space area) and when the above-described measurement period (the period during which the sensors are driven) ends.

If the measurement period is terminated, the biological sensor device 20 operates in the above-described power saving mode until an action event is detected again in the information transmitting terminal 10.

The communication module 13 included in the information transmitting terminal 10 receives the biological data transmitted by the biological sensor device 20 (specifically, the communication module 21 included in the biological sensor device 20). The biological data received by the communication module 13 is accumulated (stored) in the storage 14 (step S9).

The display processor 15 displays the biological data stored in the storage 14 in accordance with the operation by the user relative to the information transmitting terminal 10 (step S10). In this case, the biological data is displayed along with the time when the action event added to the data is generated and the time when the data is generated.

In the process shown in FIG. 6, in accordance with the action event (intake event) detected in the information transmitting terminal 10, a necessary sensor can be driven in the biological sensor device 20 only during a necessary period. Further, the biological data obtained by driving the sensor can be displayed in the information transmitting terminal 10. In this manner, it is possible to provide the user (patient) of the information transmitting terminal 10 or a doctor with the user's biological data obtained during a predetermined period after the intake of medication.

In the present embodiment, for example, if the intake event is not detected during a predetermined time period, as described above, the warning module 16 included in the information transmitting terminal 10 outputs a warning indicating that the user has forgotten to take his/her medication. This warning may be conducted by an alarm, or a warning message may be displayed in the display 111 provided in the information transmitting terminal 10. If the intake event is not sent from the information transmitting terminal 10 during a predetermined time period, the warning may be output from the biological sensor device 20 side.

Since the acceleration sensor 209 is provided in the biological sensor device 20, a tap operation relative to the biological sensor device 20 can be detected. Thus, the intake event may be detected on the biological sensor device 20 side by detecting a tap operation relative to the biological sensor device 20 although the intake event is explained as being detected in the information transmitting terminal 10 in FIG. 6. In such a case, power supply which enables the detection of a tap operation suffices for the biological sensor device 20 before the intake event is detected.

In the above descriptions, FIG. 6 is explained as follows: the user takes one type of medication (diuretic). However, in a case where the user takes a plurality of types of medications, measurement information regarding the medications is held in the biological sensor device 20 (specifically, the controller 22 included in the biological sensor device 20). In this case, when the types of medications taken by the user are transmitted to the biological sensor device 20 along with the intake event, it is possible to conduct control (for example, to drive a sensor) based on the measurement information in accordance with the intake event (that is, the types of medications taken by the user) in the biological sensor device 20. The user just has to specify the medications (or types of medications) taken by the user when the action information is obtained.

As stated above, the action information obtaining module 11 (and the action event detector 12) continues its operation after the intake event is detected. Thus, after the intake event is detected, the action information obtaining module 11 and the action event detector 12 can detect another action event although omitted in FIG. 6.

This specification now explains an operation conducted when another action event is detected after the intake event is detected (in other words, after the sensors included in the biological sensor device 20 are driven).

Action events detected by the action event detector 12 include an action in which the user goes to the bathroom (hereinafter, referred to as "bathroom use event"). The bathroom use event is detected based on information (action information) obtained by using, for example, the acceleration sensor and the microphone which are provided in the information transmitting terminal 10.

When the bathroom use event is detected in this manner, the bathroom use event is sent to the biological sensor device 20 through the communication module 13.

When the information transmitting terminal 10 transmits the bathroom use event to the biological sensor device 20, the controller 22 included in the biological sensor device 20 adds, for example, the blood pressure and heart rate as the above-described measurement items. If sensors necessary to obtain biological data indicating the blood pressure and heart rate are not included in the sensors driven based on the aforementioned intake event, the controller 22 drives the necessary sensors (for example, the electrocardiogram sensor 206 and the pulse wave sensor 207) based on the bathroom use event.

Thus, when the bathroom use event is detected in the information transmitting terminal 10, for example, it is possible to provide the user and the like with change in the biological data (blood pressure and heat rate) after the excretion of waste products through the bathroom use.

Action events detected by the action event detector 12 include a user's action in which the user moves so that the external temperature around the user is changed by a predetermined value or greater (for example, by five degrees or greater) due to the move (hereinafter, referred to as "external temperature change event"). For example, the action is to move from inside a house to outside or from outside to inside. The external temperature change event is detected based on information (action information) obtained by using, for example, the thermometer 208 provided in the information transmitting terminal 10.

When the external temperature change event is detected in this manner, the event is transmitted to the biological sensor device 20 through the communication module 13.

When the information transmitting terminal 10 transmits the external temperature change event to the biological sensor device 20, the controller 22 included in the biological sensor device 20 adds, for example, the blood pressure and heart rate as the above-described measurement items. When sensors necessary to obtain biological data indicating the blood pressure and heart rate are not included in the sensors driven based on the aforementioned intake event, the controller 22 drives the necessary sensors based on the external temperature change event (for example, the electrocardiogram sensor 206 and the pulse wave sensor 207).

When the external temperature change event is detected in the information transmitting terminal 10, it is possible to provide the user and the like with change in the biological data (blood pressure and heart rate) due to the change in external temperature.

Further, action events detected by the action event detector 12 include a user's action in which the user snores (hereinafter, referred to as "snore generation event"). The snore generation event is detected based on information (action information) obtained by using, for example, the microphone provided in the information transmitting terminal 10.

When the snore generation event is detected in this manner, the event is transmitted to the biological sensor device 20 through the communication module 13.

When the information transmitting terminal 10 transmits the snore generation event to the biological sensor device 20, the controller 22 included in the biological sensor device 20 adds, for example, the pulse wave and acceleration as the above-described measurement items. When sensors necessary to obtain the pulse wave and acceleration are not included in the sensors driven based on the aforementioned intake event, the controller 22 drives the necessary sensors (for example, the pulse wave sensor 207 and the acceleration sensor 209) based on the snore generation event.

When the snore generation event is detected in the information transmitting terminal 10, it is possible to provide the user and the like with the biological data based on the pulse wave and acceleration of the user as information for, for example, judging the apneic state of the user during sleep.

The (information of) measurement items which are added (or changed) when the above-described action events (the bathroom use event, the external temperature change event and the snore generation event) are detected are held in the controller 22 included in the biological sensor device 20 as with the above-described measurement information. Thus, in the biological sensor device 20, appropriate measurement items can be added in accordance with various action events detected in the information transmitting terminal 10.

The action events explained above are merely examples. Other action events may be detected.

In the above explanations, after the intake event is detected, another action event is detected. However, when another action event is detected before the intake event is detected, sensors necessary to obtain measurement items (biological data) based on the action event may be appropriately driven.

When the intake event is detected in the manner explained above, biological signals and biological data are obtained by driving sensors in the biological sensor device 20 as explained in FIG. 6. In this case, although omitted in FIG. 6, the biological event detector 26 included in the biological sensor device 20 can detect a biological event (an event related to the living body of the user) based on the biological signals and biological data obtained in the biological sensor device 20.

Now, this specification explains an operation conducted when a biological event is detected by the biological event detector 26. Biological events detected by the biological event detector 26 include an event in which the body temperature of the user is high or low (hereinafter, referred to as "body temperature event"). The body temperature event can be detected when the thermometer 208 which is necessary to obtain the body temperature of the user is driven. Specifically, when the body temperature of the user is, for example, equal to or higher than 37.5 degrees, a body temperature event in which the body temperature is high is detected. On the other hand, when the body temperature of the user is, for example, equal to or lower than 35.5 degrees, a body temperature event in which the body temperature is low is detected.

When a body temperature event is detected in this manner, the controller 22 included in the biological sensor device 20 increases the measurement frequency (sampling interval) of, for example, the body temperature obtained by the thermometer 208. Thus, when the body temperature of the user is higher or lower than a certain value, it is possible to provide the user and the like with change in body temperature (biological data) in more detail.

The biological events detected by the biological event detector 26 include an event in which the heart rate is increased or decreased by, for example, twenty or greater for one minute (hereinafter, referred to as "heart rate change event"). The heart rate change event can be detected when the electrocardiogram sensor 206 (pulse wave sensor 207) which is necessary to obtain the heart rate of the user is driven.

When the heart rate change event is detected in this manner, the controller 22 included in the biological sensor device 20 increases the measurement frequency of the heart rate obtained by the electrocardiogram sensor 206. Thus, the operation mode for obtaining the heart rate in the biological sensor device 20 can be switched from a mode (heart rate mode) for merely obtaining the heart rate (heartbeat interval) to a mode (electrocardiogram mode) for obtaining detailed biological data of electrocardiogram (waveform). Accordingly, when the heart rate is rapidly changed, it is possible to provide the user and the like with biological data related to the heart rate in more detail.

In the above explanations, the measurement frequency by the sensor is changed in accordance with the biological event detected by the biological event detector 26 (for example, the body temperature event or the heart rate change event). However, for example, the start or abeyance of driving of the sensor may be controlled in accordance with the biological event.

The biological events explained above are merely examples. Other biological events (for example, increase or decrease in blood pressure) may be detected.

As described above, in the present embodiment, when a user's action is detected in the information transmitting terminal 10, biological data related to the user is obtained by driving sensors in the biological sensor device 20 during the measurement period included in the measurement information in association with the action. By this configuration, in the present embodiment, sensors are driven only during a predetermined period after a user's action is detected. Therefore, the present embodiment realizes acquisition of necessary biological data and power saving in the biological sensor device 20 compared with a case in which sensors provided in the biological sensor device 20 are driven for twenty four hours. In addition, in the present embodiment, the data volume of the biological data obtained in the biological sensor device 20 can be reduced.

In the present embodiment, even if the biological sensor device 20 includes a plurality of types of sensors, only the sensors associated with the user's action detected in the information transmitting terminal 10 (in short, only the sensors which should be driven) are driven. Thus, it is possible to further reduce the power consumption of the biological sensor device 20.

In the present embodiment, biological data related to the user is obtained at the measurement frequency associated with the user's action detected in the information transmitting terminal 10. Thus, it is possible to obtain necessary biological data at an appropriate measurement frequency.

In the present embodiment, for example, the user's action (action event) in which the user took medication is detected in accordance with the operation of the user. By this configuration, it is possible to obtain biological data after the intake of medication (in other words, it is possible to accurately record the effect or side-effect of medication). Therefore, it is possible to determine whether or not the effect or side-effect of the medication taken by the user (patient) is manifest if the user (patient) confirms the information transmitting terminal 10 which displays the biological data or the user shows the information transmitting terminal 10 to a doctor.

In the present embodiment, when the action event in which the user took medication is not detected within a predetermined period, for example, a warning indicating that the user has forgotten to take his/her medication is output. In this manner, it is possible to prevent the user from forgetting to take medication.

In the present embodiment, for example, based on the biological data (or biological signal) which is obtained after the intake event is detected, the measurement frequency of the biological signal by a sensor is changed. This configuration realizes improvement in measurement accuracy when the user has a change different from usual (for example, the body temperature is high or low, or the heart rate is rapidly changed).

In the present embodiment, when the storage 25 lacks an area for storing biological data obtained in the biological sensor device 20, and when the measurement period ends, biological data stored in the storage 25 is transmitted to the information transmitting terminal 10. This transmission realizes decrease in the number of transmission times of biological data from the biological sensor device 20 to the information transmitting terminal 10. Thus, power saving is realized in the biological sensor device 20.

Figure 7:
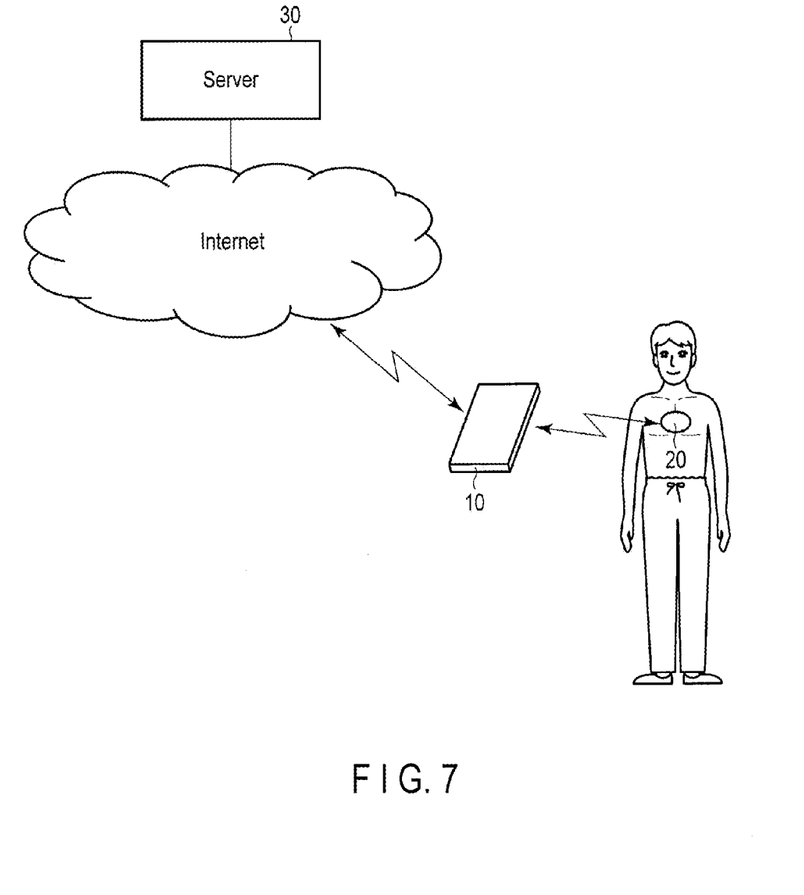
FIG. 7 is shown for explaining a case in which biological data is transmitted to a server device 30.

In the present embodiment, this specification explains that the biological data transmitted from the biological sensor device 20 to the information transmitting terminal 10 is accumulated (stored) in, for example, the storage 14 included in the information transmitting terminal 10. Further, this specification explains that the biological data is displayed in the display 111 in accordance with, for example, the instruction of the user. However, the biological data may be transmitted to (in other words, uploaded in) the external server device 30 which functions as a cloud server providing a cloud computing service as shown in FIG. 7. If biological data is managed in the server device 30 for each user (patient), for example, a doctor can download and browse the biological data of the desired user in a terminal other than the information transmitting terminal 10 (for example, in a terminal used by the doctor).

In the present embodiment, this specification merely explains the case in which the user takes medication. However, the information provision system of the present embodiment may be also applied when the effect of a medication is confirmed in, for example, a clinical trial.

This specification explains that the information provision system of the present embodiment includes the information transmitting terminal 10 and the biological sensor device 20. However, the information provision system may be realized as one device (electronic device) having both of the functions of the information transmitting terminal 10 and the biological sensor device 20.

The processes explained in the present embodiment can be executed by a computer program. Therefore, by merely installing the computer program for executing the processes in a normal computer through a computer-readable storage medium in which the computer program is stored, and executing the computer program, an effect similar to the present embodiment can be easily realized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An information provision system comprising:
   a biological sensor device including a plurality of types of sensors; and
   an information transmitting terminal communicably connected to the biological sensor device, wherein
   the information transmitting terminal includes a detector to detect an action of a user, and
   the biological sensor device includes:
      a memory to hold measurement information including a measurement period during which biological data is obtained in association with the action of the user;
      an obtaining module to obtain, when the action of the user is detected, biological data by driving the sensor during the measurement period included in the measurement information in association with the action; and
      a controller configured to change, based on a type of taken medication, a measurement frequency by a corresponding one of the types of sensors, if it is determined based on the obtained biological data that the user has a change different from usual, wherein the biological sensor device operates in a power saving mode for lower power consumption when the measurement period, which is determined according to the type of taken medication and the corresponding one of the types of sensors, is terminated.

2. The system of claim 1, wherein
the measurement information held in the memory further includes sensor information indicating a sensor to be driven in association with the action of the user, and
the obtaining module obtains the biological data by driving the sensor indicated by the sensor information included in the measurement information in association with the detected action of the user.

3. The system of claim 2, wherein
the measurement information held in the memory further includes a measurement frequency by the sensor in association with the action of the user, and
the obtaining module obtains the biological data at the measurement frequency included in the measurement information in association with the detected action of the user.

4. The system of claim 1, wherein
the action of the user includes an action in which a type of medication is taken, and
the detector detects intake of the type of medication in accordance with a user's operation of the transmitting terminal or the biological sensor.

5. The system of claim 4, wherein the information transmitting terminal further includes a warning module to output a warning when the intake of the type of medication is not detected within a predetermined period.

6. The system of claim 1, wherein
the biological sensor device further includes:
a storage in which the obtained biological data is stored; and
a communication module to transmit the biological data stored in the storage to the information transmitting terminal when the storage lacks an area for storing the obtained biological data and when the measurement period ends.

7. The system of claim 6, wherein
the information transmitting terminal further includes a display processor configured to display the transmitted biological data.

8. The system of claim 6, wherein
the information transmitting terminal further includes a communication module to transmit the transmitted biological data to an external server device.

9. The system of claim 1, wherein the action of the user includes an action in which a bathroom is used, an action in which the user moves so that an external temperature around the user is changed by a predetermined value or greater due to the move, and an action in which the user snores.

10. An electronic device including a plurality of types of sensors, the device comprising:
a detector to detect an action of a user;
a memory to hold measurement information including a measurement period during which biological data is obtained in association with the action of the user;
an obtaining module to obtain, when the action of the user is detected, biological data by driving the sensor during the measurement period included in the measurement information in association with the action; and
a controller configured to change, based on a type of taken medication, a measurement frequency by a corresponding one of the types of sensors, if it is determined based on the obtained biological data that the user has a change different from usual, wherein the electronic device operates in a power saving mode for lower power consumption when the measurement period, which is determined according to the type of taken medication and the corresponding one of the types of sensors, is terminated.

11. The device of claim 10, wherein
the measurement information held in the memory further includes sensor information indicating a sensor to be driven in association with the action of the user, and
the obtaining module obtains the biological data by driving the sensor indicated by the sensor information included in the measurement information in association with the detected action of the user.

12. The device of claim 11, wherein
the measurement information held in the memory further includes a measurement frequency by the sensor in association with the action of the user, and
the obtaining module obtains the biological data at the measurement frequency included in the measurement information in association with the detected action of the user.

13. A method executed by an information provision system including a biological sensor device and an information transmitting terminal communicably connected to the biological sensor device, the biological sensor device including a plurality of types of sensors and a memory to hold measurement information including a measurement period during which biological data is obtained in association with an action of a user, the method comprising:
detecting the action of the user by the information transmitting terminal;
obtaining, when the action of the user is detected, biological data by driving the sensor during the measurement period included in the measurement information in association with the action by the biological sensor device;
changing, based on a type of taken medication, a measurement frequency by a corresponding one of the types of sensors, if it is determined based on the obtained biological data that the user has a change different from usual, and
operating the biological sensor device in a power saving mode for lower power consumption when the measurement period, which is determined according to the type of taken medication and the corresponding one of the types of sensors, is terminated.

14. The method of claim 13, wherein
the measurement information held in the memory further includes sensor information indicating a sensor to be driven in association with the action of the user, and
the obtaining includes obtaining the biological data by driving the sensor indicated by the sensor information included in the measurement information in association with the detected action of the user.

15. The method of claim 14, wherein the measurement information held in the memory further includes a measurement frequency by the sensor in association with the action of the user, and
the obtaining includes obtaining the biological data at the measurement frequency included in the measurement information in association with the detected action of the user.

16. A non-transitory computer-readable storage medium having stored thereon a computer program which is executable by a computer of an electronic device communicably connected to a biological sensor device including a plurality of types of sensors, the program causing the computer to execute functions of:
- detecting an action of a user;
- causing the biological sensor device to obtain, when the action of the user is detected, biological data by driving the sensor during a measurement period associated with the action;
- causing the biological sensor device to change, based on a type of taken medication, a measurement frequency by a corresponding one of the types of sensors, if it is determined based on the obtained biological data that the user has a change different from usual, and
- causing the biological sensor device to operate in a power saving mode for lower power consumption when the measurement period which is determined according to the type of taken medication and the corresponding one of the types of sensors, is terminated.

17. The storage medium of claim 16, wherein
the causing includes causing the biological sensor device to obtain the biological data by driving a sensor associated with the detected action of the user.

18. The storage medium of claim 17, wherein
the causing includes causing the biological sensor device to obtain the biological data at a measurement frequency associated with the detected action of the user.

* * * * *